US011741770B2

(12) United States Patent
Wetendorf

(10) Patent No.: US 11,741,770 B2
(45) Date of Patent: Aug. 29, 2023

(54) PASSAGE DEVICE AS WELL AS METHOD FOR OPERATING SUCH A PASSAGE DEVICE

(71) Applicant: MARAYA-Holding GmbH, Siek (DE)

(72) Inventor: Ralf Wetendorf, Lütjensee (DE)

(73) Assignee: MARAYA-Holding GmbH, Siek (DE)

( * ) Notice: Subject to any disclaimer, the term of this patent is extended or adjusted under 35 U.S.C. 154(b) by 187 days.

(21) Appl. No.: 16/893,629

(22) Filed: Jun. 5, 2020

(65) Prior Publication Data

US 2021/0358248 A1    Nov. 18, 2021

(30) Foreign Application Priority Data

May 14, 2020   (DE) ...................... 10 2020 113 148.8
May 14, 2020   (EP) ...................... 20174761

(51) Int. Cl.
*G07C 9/30* (2020.01)
*G07C 9/10* (2020.01)
*E06B 5/02* (2006.01)
*A61M 35/00* (2006.01)
*G01K 1/00* (2006.01)

(52) U.S. Cl.
CPC ............... *G07C 9/30* (2020.01); *A61M 35/20* (2019.05); *E06B 5/025* (2013.01); *G01K 1/00* (2013.01); *G07C 9/10* (2020.01)

(58) Field of Classification Search
CPC ........ G05B 19/048; G05B 2219/24015; B05B 12/122
See application file for complete search history.

(56) References Cited

U.S. PATENT DOCUMENTS

| 2007/0222554 | A1 | 9/2007 | Hart | |
| 2008/0250726 | A1* | 10/2008 | Slagel | G01V 5/0008 52/79.8 |
| 2010/0308959 | A1* | 12/2010 | Schorn | G07C 9/15 340/5.2 |

(Continued)

FOREIGN PATENT DOCUMENTS

DE   102006036108   11/2007

OTHER PUBLICATIONS

European Patent Office, Extended Search Report received in International Application No. EP20174761, dated Sep. 30, 2020, 7 pp.

(Continued)

*Primary Examiner* — Huy Q Phan
*Assistant Examiner* — Temilade S Rhodes-Vivour
(74) *Attorney, Agent, or Firm* — Fitch, Even, Tabin & Flannery LLP

(57) ABSTRACT

The invention relates to a passage device comprising: at least one passage traversable by at least one person along a passage direction; at least two sidewalls spaced from each other along a direction extending perpendicularly to the passage direction, the sidewalls being connected with each other, wherein the passage is bounded along the direction by the sidewalls, and at least one capturing device by means of which a body temperature of the person located in front of at least a partial area of the passage along the passage direction can be contactlessly captured, wherein the passage device, considered on its own, is formed as a structural unit assembled and mobile.

15 Claims, 4 Drawing Sheets

(56) References Cited

U.S. PATENT DOCUMENTS

Figure 1:
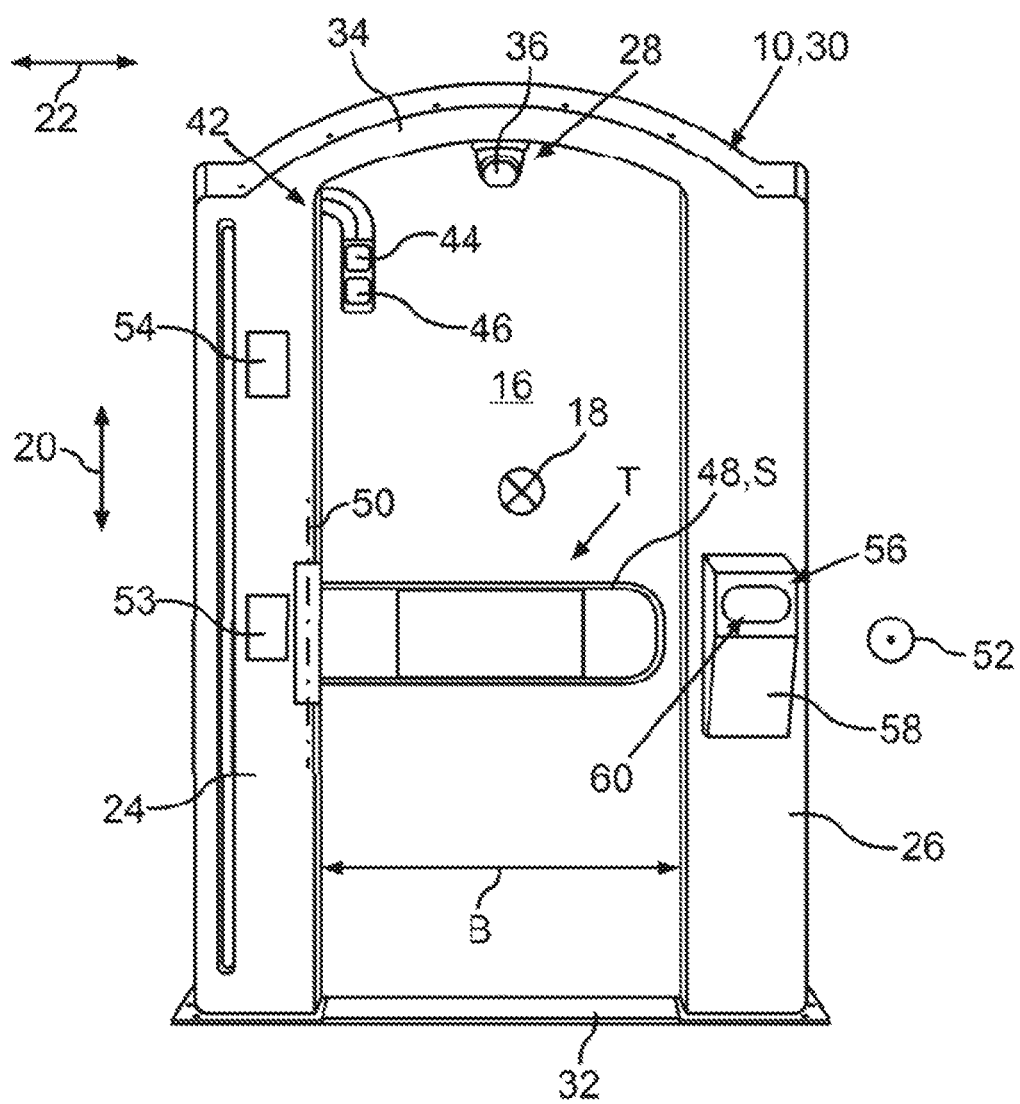

| | | | | |
|---|---|---|---|---|
| 2011/0167727 A1* | 7/2011 | Kamise | ................... | G07C 9/15 |
| | | | | 49/70 |
| 2011/0277518 A1* | 11/2011 | Lais | ........................ | G07C 9/10 |
| | | | | 340/5.83 |
| 2017/0053160 A1* | 2/2017 | Goudou | ................. | G06V 40/10 |
| 2021/0358621 A1* | 11/2021 | Castle | ................. | A61B 5/0059 |

OTHER PUBLICATIONS

Ankur Panchal, Hikvision DFMF (Door Frame 1-10 Metal Detector) With Temperature Screening Installation, Setup & Demo, https://www.youtube.com/watch?v=NzVgrNKLJZw&app=desktop, Apr. 25, 2020, 5 pp.

German Patent and Trademark Office, Examination Notice received in corresponding International Application No. 10 2020 113 148.8, dated Apr. 20, 2021, 5 pp.

\* cited by examiner

PASSAGE DEVICE AS WELL AS METHOD FOR OPERATING SUCH A PASSAGE DEVICE

CROSS-REFERENCE TO RELATED APPLICATIONS

This application claims priority from German Patent Application No. 10 2020 113 148.8, filed May 14, 2020, and European Patent Application No. 20 174 761.5, filed May 14, 2020, both of which are incorporated herein by reference in their entirety.

The present invention relates to a passage device as well as to a method for operating such a passage device. The so-called Corona pandemic now rages already since several months. Therein, the international endeavor is great to confine this pandemic and to terminate it as a result. Hereto, access or entrance controls for persons can be an important component. Within the scope of the present disclosure, by an entrance or access control, it is in particular to be understood that to at least one person who wants to proceed or move from a first spatial area into a second spatial area, access or entrance to or into the second area is allowed if and only if at least one presettable or preset criterion is satisfied. Thereby, persons, who are already in the second area, can be protected.

Therefore, it is the object of the present invention to provide a passage device and a method for operating such a passage device such that an entrance or access control can be realized in particularly simple, efficient and effective manner.

This object is solved by a passage device comprising the features of claim 1 as well as by a method comprising the features of claim 10. Advantageous configurations with convenient developments of the invention are specified in the remaining claims.

A first aspect of the invention relates to a passage device for access or entrance control. The passage device comprises at least or exactly one passage, which can be traversed by at least one person along a passage direction. This means that the person can, in particular erectly, traverse, that is go through or walk through, the passage and thus the passage device along or in the passage direction. Hereto, the passage preferably has dimensions, in particular internal dimensions, which allow the person to erectly or erectly walking traverse the passage. Therein, it is for example provided that along a first direction extending perpendicularly to the passage direction, which is also referred to as spacing or width direction, the passage has a width extending along the spacing direction, which is preferably at least 70 cm, in particular at least 100 cm and most particularly at least 120 cm. Further, it is preferably provided that along a second direction extending perpendicularly to the passage direction and perpendicularly to the spacing direction, which is also referred to as height direction, the passage has a height extending along the height direction, which is preferably at least 190 cm, in particular at least 200 cm and most particularly at least 220 cm. In installation position of the passage device, that is when the passage device occupies its position provided for its intended use, the height direction extends in vertical direction, while the spacing direction also referred to as width direction extends horizontally, that is in horizontal direction. The passage device, in particular considered in itself or on its own, for example occupies its installation position when the passage device is on an at least substantially horizontal plane, in particular such that the passage in itself, that is considered on its own, is at least 70 cm, in particular at least 100 cm and most particularly at least 120 cm wide along the width or spacing direction, and is at least 190 cm, in particular at least 200 cm and most particularly at least 220 cm high along the height direction.

Therein, the passage device comprises at least two sidewalls spaced from each other along the first direction (spacing or width direction) extending perpendicularly to the passage direction and connected to each other, by which the passage is bounded along the width or spacing direction. The respective sidewall is preferably inherently rigid, that is dimensionally stable.

In addition, the passage device includes at least one capturing device by means of which a body temperature of the person located in front of at least a partial area of the passage, in particular in front of the entire passage, along the passage direction can be contactlessly captured. By the feature that the body temperature of the person can be contactlessly captured by means of the capturing device, it is to be understood that the body temperature of the person can be captured in contactless manner related to the person by means of the capturing device. In other words, the capturing device is formed to capture, that is to measure, the body temperature of the person without contact between the person and the capturing device, in particular the passage device as a whole, occurring. Again expressed in other words, the passage device can capture, that is measure, the body temperature of the person by means of the capturing device without contact between the person and the passage device occurring therein.

In order to be able to particularly simply, efficiently and effectively realize the above mentioned entrance or access control by means of the passage device, it is further provided that the passage device is formed as a structural unit assembled and mobile considered on its own. This means that the passage device for example can overall, that is as a whole, be transported and/or handled and thus for example be established, that is positioned, between two areas in particularly simple manner. Therein, the passage device allows to allow to the person, who for example wants to get from a first one of the areas into the second area, access or entrance to the or into the second area if and in particular only if at least one in particular preset or presettable criterion is satisfied. In particular, the passage device can be positioned or established in particular in its installation position relative to the mentioned areas such that a or the person, who for example wants to move from the first area into the second area, in particular wants to go from the first area into the second area, has to move through the passage, in particular go through the passage. Access or entrance to the or into the second area is for example allowed to the person if and only if it is ascertained by means of the capturing device or by means of the passage device that the body temperature of the person captured by means of the capturing device is lower than a preset or presettable threshold value. In other words, the above mentioned criterion is the body temperature of the person, wherein the criterion is satisfied if the body temperature is below the threshold value.

Since the passage device according to the invention is formed as a structural unit assembled and mobile, that is transportable, considered on its own, the passage device according to the invention can be adequately and simply transported to different locations, in particular as a whole, and be established or arranged there, in particular between two areas. Thereby, effective and efficient entrance or access controls can be realized in particularly simple manner. By the feature that the passage device is mobile or a mobile structural unit, it is in particular to be understood that the passage device can be reversibly, that is non-destructively, removed from respective locations, at which an entrance or access control was realized by means of the passage device, and transported to other locations. This in particular includes that the passage device is not anchored or does not have to be anchored to a floor for instance by means of a foundation for example formed of concrete at the respective location, but the passage device according to the invention can for example be simply established, reversibly, that is non-destructively, detachably secured against undesired movements and thereupon again detached and removed from the respective location and transported to another location. Thus, the passage device according to the invention is in particular suitable for realizing entrance or access controls for non-permanent, that is transient, happenings, such as for example events. Such events can for example be concerts, public festivals, cultural events and/or sport events. Thus, a use of the passage device according to the invention preferably also belongs to the invention, wherein the passage device according to the invention is used to for example perform an entrance or access control by means of the passage device during a transient happening.

In order to be able to particularly simply handle and transport and thus position the passage device at different locations, to be able to perform an entrance or access control at these locations, it is provided in a configuration of the invention that the passage device comprises a preferably inherently rigid or dimensionally stable floor bounding the passage downwards, wherein the sidewalls are connected to each other via the floor. By the feature that the passage is bounded downwards by means of the floor, it is in particular to be understood that the passage is downwards bounded by the floor in height direction or in vertical direction in installation position of the passage device. For example, the floor is at least indirectly, in particular directly, connected to the sidewalls such that the sidewalls are connected to each other via the floor. Thus, the passage or the passage device can be formed in the shape of a U open to the top in vertical direction.

It has proven further particularly advantageous if the passage device comprises a ceiling element bounding the passage upwards, wherein the ceiling element is preferably inherently rigid or dimensionally stable. The sidewalls are connected to each other via the ceiling element. Hereto, the ceiling element is for example at least indirectly, in particular directly, connected to the sidewalls. Hereby, the passage device can be particularly simply handled and transported such that respective entrance or access controls can be performed by means of the passage device at different locations in particularly simple, efficient and effective manner.

In order to be able to particularly advantageously measure the body temperature of the person, it is provided in an embodiment of the invention that the capturing device is held on the ceiling element. Hereby, the head of the person can be particularly well captured for example by means of the capturing device such that the body temperature can be measured based on the head, in particular based on the forehead, of the person. In addition, a particularly advantageous mobility and thus transportability of the passage device can be presented by the arrangement of the capturing device at the ceiling element.

In a further, particularly advantageous embodiment of the invention, it is provided that the passage device comprises an access control device arranged at least in front of the partial area of the passage, in particular in front of the entire passage, along the passage direction. Thus, the access control device is preferably a component of the mobile passage device and can be transported and established together with the passage device such that a particularly advantageous, mobile usability of the passage device can be presented. The access control device is also referred to as entrance control device and is for example formed to allow and to prevent, respectively, an access or entrance of the person to the or into the partial area of the passage and thus for example to the or into the above mentioned second area depending on the captured body temperature. In other words, if the captured body temperature is for example below the threshold value, thus, the access control device releases the access to the partial area of the access for the person. However, if the captured body temperature corresponds to the threshold value or if the captured body temperature is above the threshold value, thus, the access control device for example mechanically blocks the access to the or into the partial area for the person such that the person cannot go or get into the partial area and thus into the above mentioned second area.

Therein, it has proven particularly advantageous if the access control device comprises at least one lighting device, which is formed to emit at least light with a color. The light and in particular the color thereof is perceivable by the human eye. If the color is for example green, thus, the access control device for example releases the access to the partial area of the passage in that the lighting device emits the light. If emission of the light is omitted, thus, the access control device denies the access to the partial area to the person. If the color is for example red, thus, the access control device for example allows the access into the partial area to the person in that an emission of the light is omitted. The access to the partial area is for example denied to the person in that the lighting device emits the red light.

Therein, it has proven particularly advantageous if the access control device comprises at least a second lighting device, which is formed to emit light with a second color different from the first color. The first color is for example red, wherein the second color is for example green. For example, the first lighting device first emits the light in the first color (red), while emission of the light with the second color is omitted. Then, the body temperature is for example captured. If the body temperature is below the threshold value, thus, the emission of the light with the first color (red) is terminated, and the second lighting device emits the light with the second color (green). Thereby, the access to the or into the partial area is allowed to the person. However, if the body temperature is above the threshold value or if the body temperature corresponds to the threshold value, thus, the first lighting device further emits the light with the first color, while emission of the light with the second color is omitted. Thereby, the access into the partial area is denied. Since the access control device and as a result the lighting device or the lighting devices are components of the mobile structural unit, an effective and efficient entrance or access control can be adequately realized at different locations by means of the passage device in particularly simple manner.

A further embodiment is characterized in that the access control device comprises at least one, in particular dimensionally stable or inherently rigid, blocking element which is movable, in particular pivotable, between a blocking position and at least one release position relative to the sidewalls as well as preferably relative to the floor and/or relative to the ceiling element. In the blocking position, the blocking element overlaps or covers at least a part of the partial area of the passage in a third direction opposite to the passage direction such that the person standing in front of the partial area along the passage direction can for example not simply erectly go into the partial area. The person is prevented from it by the in particular mechanical blocking element. However, in the release position, the blocking element releases the mentioned part of the partial area of the passage such that the person first located in front of the partial area of the passage can then erectly go into the partial area and thereby pass the blocking element. Hereby, an entrance or access control can be realized in particularly effective and efficient manner. Since the blocking element is a component of the mobile structural unit, the blocking element is transported and established or constructed as well as dismantled together with the structural unit. Thereby, entrance or access controls can be realized by means of the passage device according to the invention at different locations in particularly simple manner.

Overall, it is apparent that for example with regard to the current Corona pandemic, but also with regard to possible, further pandemics or epidemics, such entrance or access controls can be realized by means of the passage device according to the invention that persons with elevated body temperature and thus persons suffering from fever can be prevented from getting from the above mentioned first area into the above mentioned second area in simple, effective and efficient manner. Therein, the invention is in particular based on the realization that an elevated body temperature can be an indication of a for example infectious disease of the person. In that the access into the second area is denied to the person, if the body temperature exceeds the threshold value or corresponds to the threshold value, persons already located in the second area can for example be protected from a contact with the person, whereby it can for example be avoided that the person infects the further persons. Hereby, an extensive and uncontrolled propagation of a disease can for example be securely and simply avoided.

Therein, it has proven particularly advantageous if the passage device comprises at least one provision device, which comprises at least one chamber, in which a fluid, in particular a liquid, can be received or is received. In particular, the fluid can be a gel. Preferably, the fluid is a disinfectant, in particular a chemical disinfectant, which is in particular formed to reduce germs, in particular by at least 90%.

Preferably, the provision device is formed to provide the fluid from the chamber as a result of an, in particular contactless, interaction between the person and the provision device, in particular to convey and/or spray it into an environment of the provision device, in particular the passage device as a whole. By the feature that the provision device is formed to provide the fluid from the chamber as a result of a contactless interaction between the person and the provision device, it is in particular to be understood that the provision device is formed to provide the fluid without a contact between the person and the provision device, in particular between the person and the passage device as a whole, being required or being performed hereto. Hereto, the provision device for example comprises a movement sensor, which is formed to capture that the person moves and holds at least one of her body parts, in particular one of her hands, below at least one opening of the provision device. As a result, the provision device provides the fluid from the chamber for example such that the provision device conveys the fluid from the chamber through the opening and thus conveys it to the environment. Hereby, the fluid is conveyed from the chamber for example at least to a part of the hand of the person. As a result, the person can rub the fluid in her hands and thus disinfect the hands.

Alternatively or additionally, the provision device is formed to provide at least one nose and/or mouth protective mask. Hereto, the provision device for example comprises a store, in which at least one or preferably multiple protective masks are received. The respective protective mask is a nose and/or mouth protective mask, by means of which the person can cover her nose and/or her mouth. The provision device can provide the respective protective mask for example such that the person can manually remove the respective protective mask from the store. Further, it is conceivable that the provision device is formed to provide the respective protective mask as a result of a contactless interaction between the person and the provision device, in particular such that the provision device conveys the respective protective mask out of the store as a result of the interaction and for example conveys it to the environment of the provision device, in particular of the passage device as a whole. As a result, the person can apply or put on the protective mask and thus protect her nose and/or her mouth. Thereby, an excessive extensive distribution of saliva and germs, respectively, in the second area can be avoided for example if the person speaks and/or sneezes.

In order to be able to particularly effectively and efficiently capture the body temperature, it is provided in further configuration of the invention that the capturing device comprises at least or exactly one thermal imaging camera for capturing the body temperature.

A second aspect of the invention relates to a method for operating a passage device according to the first aspect of the invention. Advantages and advantageous configurations of the first aspect of the invention are to be regarded as advantages and advantageous configurations of the second aspect of the invention and vice versa.

The method in particular includes that the capturing device provides at least one, in particular electrical, signal, which characterizes the body temperature captured by means of the capturing device. For example, the passage device includes an electronic computing device, which receives the above mentioned signal. Depending on the received signal, the electronic computing device for example provides an, in particular electrical, control signal, by means of which the electronic computing device for example controls the access control device. For example, the respective lighting device is controlled by means of the control signal such that the respective lighting device for example provides the respective light depending on the signal. Alternatively or additionally, a motor in particular formed as an electric motor is for example controlled by means of the control signal, by which the blocking element is movable between the release position and the blocking position. For example, the electronic computing device compares the captured body temperature of the person characterized by the signal to the threshold value. If the electronic computing device ascertains that the captured body temperature is lower than the threshold value, the electronic computing device for example controls the respective lighting device and the motor such that the emission of the light with the first color (red) is terminated, the second lighting device emits the light with the second color (green) and/or the motor moves the blocking element from the blocking position into the release position. Thereby, the access or entrance into the partial area of the passage and as a result into the second area is allowed, that is permitted, to the person.

Further advantages, features and details of the invention are apparent from the following description of preferred embodiments as well as based on the drawing. The features and feature combinations mentioned above in the description as well as the features and feature combinations mentioned below in the description of figures and/or shown in the figures alone are usable not only in the respectively specified combination, but also in other combinations or alone without departing from the scope of the invention.

THE DRAWING SHOWS IN

Figure 2:
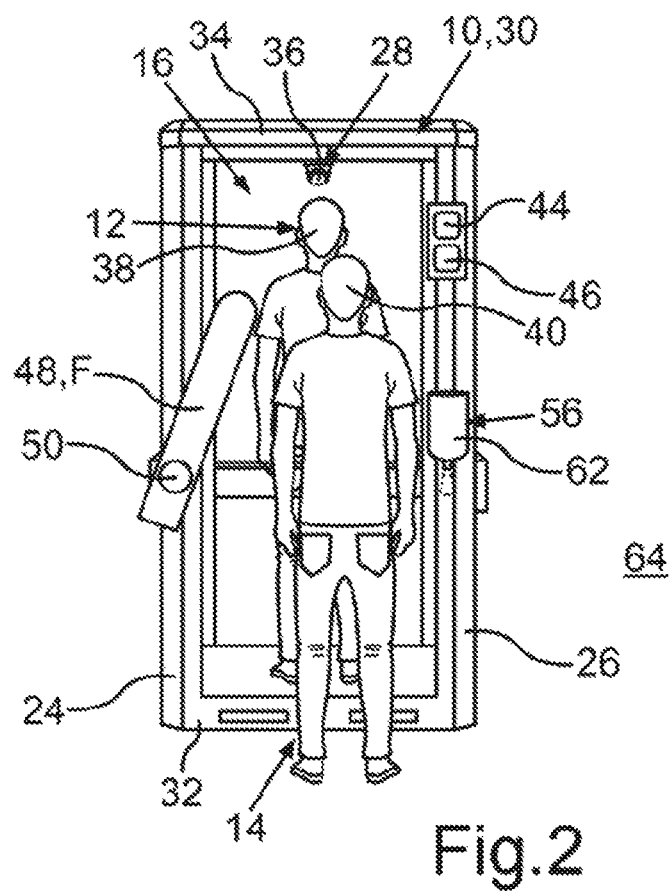
Figure 3:
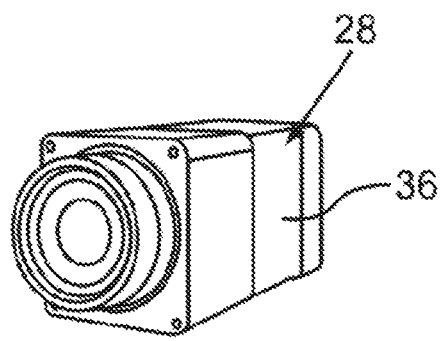
Figure 4:
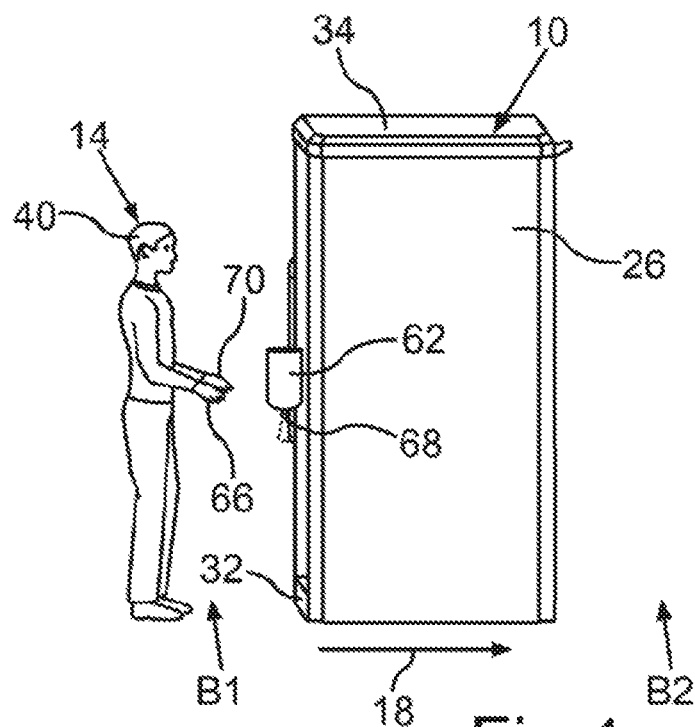
Figure 5:
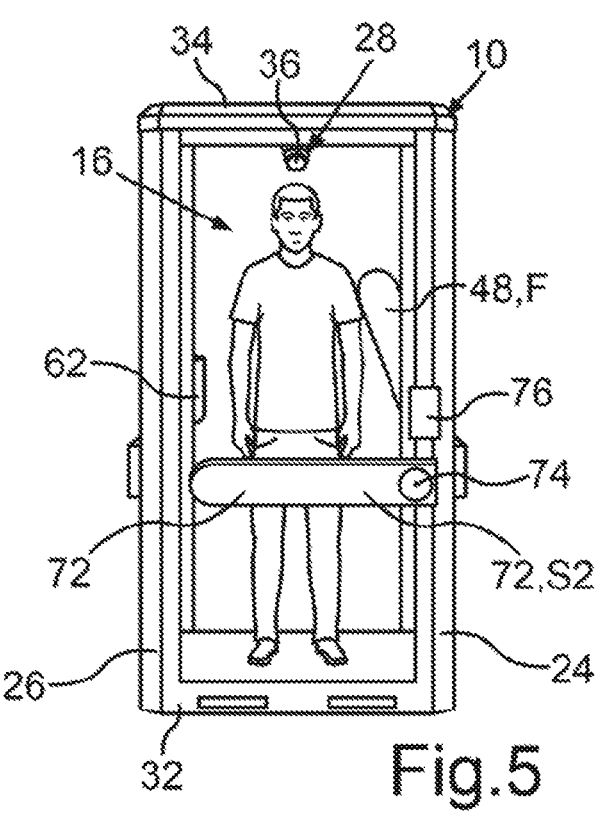
Figure 6:
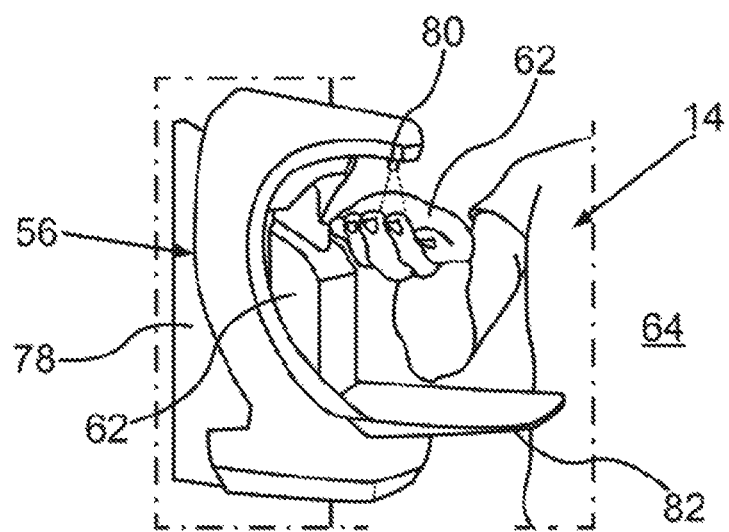
Figure 7:
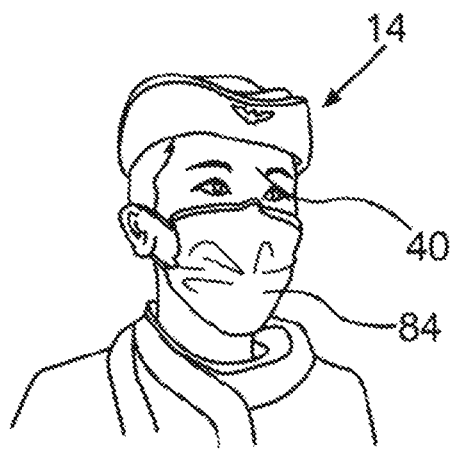

FIG. 1 a schematic front view of a passage device according to the invention according to a first embodiment;

FIG. 2 a schematic front view of the passage device according to a second embodiment;

FIG. 3 a schematic perspective view of a thermal imaging camera of a capturing device of the passage device;

FIG. 4 a schematic side view of the passage device according to the second embodiment;

FIG. 5 a schematic rear view of the passage device according to the second embodiment;

FIG. 6 a schematic perspective view of a provision device of the passage device; and FIG. 7 a schematic perspective view of a head of a person.

In the figures, identical or functionally identical elements are provided with identical reference characters.

FIG. 1 shows a first embodiment of a passage device 10 in a schematic front view. The passage device 10 comprises a passage 16 traversable by persons 12, 14 (FIG. 2) along a passage direction. This means that the persons 12 and 14 can erectly traverse, that is go through, the passage 16 if the passage device 10 releases the passage 16. The above mentioned passage direction is illustrated by an arrow 18 in FIG. 1, wherein the passage direction extends perpendicularly to the image plane of FIG. 1 and therein points away from a respective observer of FIG. 1. The figures show the passage device 10 in its installation position, that is in its position provided for its intended use. Therein, the double arrow 20 illustrates the vertical direction, while a double arrow 22 horizontally extends, that is illustrates the horizontal direction. Therein, it is apparent that the passage direction also horizontally extends. In particular, the double arrow 22 illustrates a first direction, which is also referred to as spacing direction and/or width direction. The double arrow 20 illustrates a second direction, which is also referred to as height direction. The passage direction extends perpendicularly to the first direction and perpendicularly to the second direction, wherein the second direction extends perpendicularly to the first direction. The passage device 10 comprises two inherently rigid sidewalls 24 and 26 spaced from each other along the first direction (double arrow 22) extending perpendicularly to the passage direction and connected to each other, by which the passage 16 is, in particular completely, bounded along the first direction (width direction). Thus, the passage 16 has a width B extending along the width direction. The width B is a distance between the sidewalls 24 and 26 extending along the width direction. Preferably, the width B is at least 70 cm, in particular at least 90 cm and most particularly at least 110 cm.

In addition, the passage device 10 comprises a capturing device 28, by means of which a respective body temperature of the respective person 12 and 14, respectively, located in front of at least a partial area of the passage 16, in particular in front of the entire passage 16, along the passage direction can be or is contactlessly captured. Therein, the passage device is formed as a structural unit 30 assembled and mobile considered on its own. This means that the passage device 10 or the structural unit 30 can be transported and reversibly, that is non-destructively, detachably established or positioned at respective locations, at which a respective entrance or access control can be realized by means of the passage device 10 in particularly simple, efficient and effective manner, as a whole and in particular in the assembled state, which is shown in the figures. In synopsis with FIG. 4, it is apparent that the passage device 10 can be arranged or positioned at the respective location in particular such that the passage device 10 can be arranged between a first area B1 and a second area B2, in particular along the passage direction. The area B1 is arranged in front of the area B2 along the passage direction illustrated by the arrow 18. The respective person 12 and 14, respectively, who wants move from the first area B1 into the second area B2, in particular go from the area B1 into the area B2, has to move, that is in particular walk or go, through the passage 16 and thus through the passage device 10 along the passage direction— to get from the area B1 into the area B2. However, the respective person 12 and 14, respectively, can go through the passage 16 and thus get from the area B1 into the area B2 if and only if—as will be explained in more detail in the following—the passage device 10 releases its passage 16 for the person 12 and 14, respectively.

FIG. 1 shows a first embodiment of the passage device 10. Therein, the passage device 10 comprises a preferably inherently rigid floor 32 downwards bounding the passage 16 along the second direction or in vertical direction, via which the sidewalls 24 and 26 are connected to each other. In the first embodiment, the floor 32 is formed separately from the sidewalls 24 and 26 and connected to the sidewalls 24 and 26. In addition, the passage device 10 comprises a preferably inherently rigid ceiling element 34, by which the passage 16 is, in particular completely, upwards bounded along the second direction and thus in vertical direction. Therein, the sidewalls 24, 26 are connected to each other via the ceiling element 34. In the first embodiment, it is provided that the ceiling element 34 is formed integrally with the sidewalls 24 and 26. For example, the sidewalls 24, 26 and the ceiling element 34 are formed by an integral plastic part, in particular by an integral plastic injection molding part. Thus, the passage device 10 is for example formed in the manner of an archway or a little house. Further, it is conceivable that the ceiling element 34 is formed separately from the sidewalls 24, 26 and connected to the sidewalls 24, 26.

The capturing device 28 is held on the ceiling element 34. As is apparent in synopsis with FIG. 3, the capturing device 28 includes at least or exactly one thermal imaging camera 36, by means of which at least the respective head 38 and 40, respectively, of the respective person 12 and 14, respectively, located in front of the passage 16 along the passage direction can for example be captured. In particular, a respective temperature of the respective head 38 and 40, respectively, can be captured by means of the thermal imaging camera 36, wherein the captured temperature is the body temperature.

The passage device 10 and thus the mobile structural unit 30 additionally includes an access control device 42, which is arranged at least in front of the mentioned partial area of the passage 16 along the passage direction. In the embodiment shown in FIG. 1, the access control device 42 comprises a first lighting device 44, which is formed to emit light with a first color. The first color is for example red. Furthermore, the access control device 42 includes a second lighting device 46, which is formed to emit light with a second color different from the first color. Preferably, the second color is green. The light and the color, respectively, are perceivable by the human eye.

In addition, the access control device 42 includes an inherently rigid blocking element 48 for example formed as a bracket, which is movable, in particular pivotable around a pivot axis, between a blocking position S and at least one release position F (FIG. 2) relative to the sidewalls 24 and 26 and presently also relative to the floor 32 and relative to the ceiling element 34. The mentioned pivot axis is denoted by 50 and extends perpendicularly to the passage direction and therein in vertical direction or along the second direction in the first embodiment.

FIGS. 2 to 5 show a second embodiment of the passage device 10. In the second embodiment, the pivot axis extends parallel to the passage direction. In the blocking position S, the blocking element 48 overlaps at least a part T of the passage 16 in a third direction opposite to the passage direction and illustrated by an arrow 52 in FIG. 1. The third direction extends perpendicularly to the image plane of FIG. 1 and towards the respective observer of FIG. 1. In the release position F, the blocking element 48 releases the part T such that the part T is no longer overlapped or covered by the blocking element 49 in the third direction in the release position F. Thus, while the blocking element 48 prevents the respective person 12 and 14, respectively, standing in front of the passage 16 along the passage direction from erectly going through the passage 16 in the blocking position, the blocking element 48 releases the passage 16 for the respective person 12 and 14, respectively, in the release position F such that the respective person 12 and 14, respectively, can then erectly go through the passage 16.

Therein, the passage device 10 or the structural unit 30 includes a motor 53 preferably formed as an electric motor, by means of which the blocking element 48 is movable between the blocking position S and the release position F using electrical energy or electrical current. Furthermore, it can be provided that the passage device 10 or the structural unit 30 comprises an electronic computing device 54, which is also referred to as control device or control unit. In the following, a method for operating the passage device 10 is described.

First, both persons 12 and 14 are for example standing in front of the passage 16 along the passage direction. Therein, the person 12 stands in front of the person 14 such that the person 12 stands between the blocking element 48 and the person 14 along the passage direction. Therein, the blocking element 48 is first in the blocking position S and the lighting device 44 emits the light with the first color, while emission of the light with the second color by the lighting device 46 is omitted.

By means of the capturing device 28, in particular by means of the thermal imaging camera 36, the body temperature of the person 12 is contactlessly captured. The capturing device 28 provides an, in particular electrical, signal, which characterizes the body temperature of the person 12 captured by means of the capturing device 28. The electronic computing device 54 receives the signal and compares the captured body temperature to a for example preset or presettable threshold value, which is for example stored in a memory of the electronic computing device 54. If the electronic computing device 54 ascertains that the body temperature of the person 12 corresponds to the threshold value or is greater than the threshold value by comparing the captured body temperature of the person 12 to the threshold value, thus, the blocking element 48 remains in the blocking position S, the lighting device 44 further emits the light with the first color and emission of the light with the second color by the lighting device 44 is omitted. Thus, the access into the area B2 is denied to the person 12. However, if the electronic computing device 54 ascertains that the body temperature of the person 12 first located in the area B1 is less than the threshold value, thus, the electronic computing device 54 controls the access control device 42 in particular by means of at least one, in particular electrical, control signal such that the emission of the light with the first color by the lighting device 44 is terminated, the lighting device 46 emits the light with the second color and the blocking element 48 is moved, in particular pivoted, from the blocking position S into the release position F, by means of the motor 53. As a result, the person 12 can erectly go through the passage 16 and thus go from the area B1 via the passage 16 into the area B2. Thereupon—still before the person 14 can traverse the passage 16—the blocking element 48 is moved from the release position F into the blocking position S by means of the motor 53, the emission of the light with the second color by the lighting device 46 is terminated and the lighting device 44 emits the light with the first color. Hereby, the access to the passage 16 and in particular to the area B2 is first denied to the person 14. Thereupon, the body temperature of the person 14 is captured by means of the capturing device 28, in particular by means of the thermal imaging camera 36. The electronic computing device 54 compares the body temperature of the person 14 to the threshold value. If the body temperature of the person 14 is above the threshold value or if the body temperature of the person 14 corresponds to the threshold value, thus, the access to the passage 16 and to the area B2 is denied to the person 14. However, if the body temperature of the person 14 is also below the threshold value, thus, the blocking element 48 is moved from the blocking position S into the release position F by means of the motor 53, the emission of the light with the first color by the lighting device 44 is terminated and the lighting device 46 emits the light with the second color. Hereby, the passage 16 is also released for the person 14 such that the person 14 can erectly walk through the passage 16 and as a result can walk from the area B1 into the area B2. It is apparent that a particularly simple, effective and efficient access or entrance control can be presented by the passage device 10.

In the first embodiment, the passage device 10 or the structural unit 30 includes a provision device 56. In the first embodiment, the provision device 56 is for example formed to provide at least one or multiple protective masks for the respective person 12 and 14, respectively. For example, the protective mask is a nose and/or mouth protective mask, which can be attached to the respective head 38 and 40, respectively, by the respective person 12 and 14, respectively, such that the protective mask covers the mouth and/or the nose of the respective person 12 and 14, respectively. Hereto, the provision device 56 comprises a container 58 with a receiving space 60 for example formed as a store, in which the protective masks can be or are received. The respective person 12 and 14, respectively, can for example manually remove the respective protective mask from the receiving space 60 and subsequently put it on.

In particular, it can be provided that the respective lighting device 44 and 46, respectively, is held on one of the sidewalls 24 and 26. Alternatively or additionally, the blocking element 48 is for example movably held on one of the sidewalls 24, 26.

In the second embodiment, the provision device 56 includes a vessel 62 with a chamber not apparent in the figures. A preferably liquid fluid can be or is received in the chamber and thus in the vessel 62, which is preferably formed as a disinfectant. Therein, the provision device 56 is preferably formed to provide the fluid from the chamber as a result of a contactless interaction between the respective person 12 and 14, respectively, and the provision device 56, in particular to convey, in particular spray, it to an environment 64 of the provision device 56, in particular of the passage device 10 as a whole.

As shown in FIG. 4 on the example of the person 14, the person 14 can for example move and hold her hand 66 below the vessel 62. This movement is recognized by means of the provision device 56, whereupon the fluid is sprayed from the chamber to the environment 64 without the person 14 contacting the passage device 10. The fluid, which is apparent in FIG. 4 and denoted by 68 there, is sprayed onto the hand 66. As a result, the person 14 can rub the fluid in her hands 66 and 70. Thereby, the hands 66 and 70 are disinfected. The same can be transferred to the person 12.

FIG. 5 shows the passage device 10 according to the second embodiment in a schematic rear view. It is apparent that the passage device 10 comprises a second blocking element 72 provided in addition to the blocking element 48. The blocking element 72 is also movable, in particular pivotable, between a respective second blocking position S2 and at least one second release position relative to the sidewalls 24 and 26. In the second embodiment, the blocking element 72 is pivotable around a second pivot axis 74 between the second release position and the second blocking position S2 relative to the sidewalls 24, 26, wherein the second pivot axis 74 extends parallel to the first pivot axis S or coincides with the first pivot axis S. The blocking elements 48 and 72 can for example be moved, in particular pivoted, independently of each other. Hereby, it is in particular to be understood that the blocking element 48 can be moved or pivoted, while moving or pivoting the blocking element 72 is omitted. Alternatively or additionally, the blocking element 72 can be moved or pivoted while moving or pivoting the blocking element 48 is omitted.

In the second blocking position S2, at least a further part of the partial area of the passage 16 or the above mentioned part T of the partial area of the passage is overlapped or covered by the blocking element 72 in the passage direction. In the second release position, the blocking element 72 releases the further part or the part T such that the person 12 and 14, respectively, located in the passage 16 is for example first prevented from going out of the passage 16 and going into the area B2 by means of the blocking element 72 located in the second blocking position S2. However, if the blocking element 72 is in the second release position, thus, the respective person 12 and 14, respectively, first located in the passage 16 can erectly go out of the passage 16 and go into the area B2. Thus, the blocking element 72 is arranged behind the partial area of the passage 16 or behind the entire passage 16 along the passage direction in the second blocking position S2. Thus, it is for example conceivable to first move the blocking element 48 from the blocking position S into the release position F, while the blocking element 72 is located in the second blocking position S2. If the person 12 and 14, respectively, thereupon has walked into the passage 16, thus, the blocking element 48 is for example first moved from the release position F into the blocking position S while the blocking element 72 is still in the second blocking position S2. Only thereupon, the blocking element 72 is moved from the second blocking position S2 into the second release position F, such that the person 12 and 14, respectively, first located in the passage 16 can then walk out of the passage 16 and walk into the area B2. Thereby, it can for example be prevented that the two persons 12 and 14, who optionally have together gone into the passage 16, can commonly or together go from the passage 16 into the area B2.

Therein, the passage device 10 for example includes a further motor 76 provided in addition to the motor 53 and particularly schematically illustrated in FIG. 5, which can for example be formed as a further electric motor. Therein, the electronic computing device 54 can for example control the motor 76, in particular depending on time, to move the blocking element 72 between the second release position and the second blocking position S2 by means of the motor 76 as a result. Further, it is conceivable that the motor 53 is a motor common to the blocking elements 48 and 72, by means of which the blocking elements 48 and 72 are movable between the respective blocking positions and release positions, in particular commonly or consecutively in time.

FIG. 6 shows the provision device 56 in a schematic perspective view, which is formed for providing the fluid. Therein, the vessel 62 is for example reversibly detachably held on a base 78 such that the vessel 62, when it is empty, can be simply replaced with other, further containers. A provision element 80 of the provision device 56 is apparent from FIG. 6. The provision element 80 comprises an opening, via which the fluid can be conveyed from the vessel 62 to the environment 64. A collecting element 82 for example formed as a collecting pan is arranged below the opening of the provision element 80 in vertical direction, by means of which or in which excessive fluid from the vessel 62 can be collected.

Finally, FIG. 7 shows the person 14 and in particular the head 40 thereof in a schematic perspective view, wherein the person 14 has removed a protective mask denoted by 84 from the provision device 56, in particular from the container 58, and has applied it such that the protective mask 84 covers both the mouth and the nose of the person 14. By means of the provision device 56, it is possible to avoid importing of an excessive amount of germs from the area B1 into the area B2. In addition, an excessive distribution of germs, for example by saliva, in the area B2 can be avoided.

The invention claimed is:

1. A passage device, comprising:
   at least one passage traversable by at least one person along a passage direction;
   at least two sidewalls spaced from each other along a second direction extending perpendicularly to the passage direction, the sidewalls being connected with each other, wherein the passage is bounded along the second direction by the sidewalls, and
   at least one capturing device by means of which a body temperature of a person located in front of at least a partial area of the passage along the passage direction can be contactlessly captured, wherein the passage device, considered on its own, is formed as a structural unit that is assembled and mobile, and wherein the passage device comprises a ceiling element bounding the passage upwards, wherein the sidewalls are connected to each other via the ceiling element, and wherein the capturing device is held on the ceiling element.

2. The passage device according to claim 1, wherein the passage device comprises a floor bounding the passage at a lower end, wherein the sidewalls are connected to each other via the floor.

3. The passage device according to claim 1, wherein the passage device comprises an access control device arranged at least in front of the partial area of the passage along the passage direction.

4. The passage device according to claim 3, wherein the access control device comprises at least one lighting device configured to emit at least one light with a color.

5. The passage device according to claim 3, wherein the access control device comprises at least one blocking element movable relative to the sidewalls between a blocking position in which the blocking element overlaps at least a part of the partial area of the passage in a direction opposite to the passage direction, and at least one release position uncovering the part.

6. The passage device according to claim 1, wherein the passage device comprises at least one provision device comprising at least one chamber in which a fluid can be or is received, wherein the provision device is configured to provide the fluid from the chamber as a result of an interaction between the person and the provision device.

7. The passage device of claim 6, wherein the provision device is configured to provide the fluid from the chamber as a result of a contactless interaction between the person and the provision device.

8. The passage device of claim 6, wherein the provision device is configured to spray the fluid from the chamber into an environment of the provision device.

9. The passage device according to claim 1, wherein the capturing device comprises at least one thermal imaging camera for capturing the body temperature.

10. A method for operating a passage device according to claim 1, the method comprising capturing, without contact, a body temperature of the person located in front of at least the partial area of the passage.

11. A passage device, comprising:
at least one passage traversable by at least one person along a passage direction;
at least two sidewalls spaced from each other along a direction extending perpendicularly to the passage direction, the sidewalls being connected with each other, wherein the passage is bounded along the direction by the sidewalls,
at least one capturing device by means of which a body temperature of the person located in front of at least a partial area of the passage along the passage direction can be contactlessly captured, wherein the passage device, considered on its own, is formed as a structural unit assembled and mobile; and
at least one provision device comprising at least one chamber in which a fluid can be or is received, wherein the provision device is configured to provide the fluid from the chamber as a result of a contactless interaction between the person and the provision device.

12. The passage device according to claim 11, wherein the passage device comprises a ceiling element bounding the passage upwards, wherein the sidewalls are connected to each other via the ceiling element.

13. The passage device of claim 11, wherein the provision device is configured to spray the fluid from the chamber into an environment of the provision device.

14. The passage device of claim 11, wherein the capturing device comprises at least one thermal imaging camera for capturing the body temperature.

15. A method for operating a passage device comprising:
at least one passage traversable by at least one person along a passage direction;
at least two sidewalls spaced from each other along a direction extending perpendicularly to the passage direction, the sidewalls being connected with each other, wherein the passage is bounded along the direction by the sidewalls,
at least one capturing device by means of which a body temperature of the person located in front of at least a partial area of the passage along the passage direction can be contactlessly captured, wherein the passage device, considered on its own, is formed as a structural unit assembled and mobile, wherein the passage device comprises a ceiling element bounding the passage upwards, wherein the sidewalls are connected to each other via the ceiling element, and wherein the capturing device is held on the ceiling element,
an access control device arranged at least in front of the partial area of the passage along the passage direction, wherein the access control device comprises at least one blocking element movable relative to the sidewalls between a blocking position in which the blocking element overlaps at least a part of the partial area of the passage in a direction opposite to the passage direction (18), and at least one release position uncovering the part, and
an electronic computing device wherein:
the capturing device provides at least one electrical signal, which characterizes the body temperature,
the electronic computing device receives the signal,
the electronic computing device compares the captured body temperature characterized by the signal to a threshold value, and
if the electronic computing device ascertains that the captured body temperature is lower than the threshold value, the electronic computing device controls the motor such that the motor moves the blocking element from the blocking position into the release position.

* * * * *